US010123699B2

(12) United States Patent
Sakagawa et al.

(10) Patent No.: US 10,123,699 B2
(45) Date of Patent: Nov. 13, 2018

(54) OPHTHALMOLOGIC APPARATUS AND IMAGING METHOD

(71) Applicant: CANON KABUSHIKI KAISHA, Tokyo (JP)

(72) Inventors: Wataru Sakagawa, Kawasaki (JP); Marek Rozanski, Torun (PL); Tomasz Dziubak, Torun (PL)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/451,672

(22) Filed: Mar. 7, 2017

(65) Prior Publication Data

US 2017/0258326 A1 Sep. 14, 2017

(30) Foreign Application Priority Data

Mar. 10, 2016 (JP) ................................ 2016-046795

(51) Int. Cl.
*A61B 3/12* (2006.01)
*A61B 3/00* (2006.01)
*A61B 3/10* (2006.01)
*A61B 3/113* (2006.01)
*A61B 3/15* (2006.01)

(52) U.S. Cl.
CPC .......... *A61B 3/1233* (2013.01); *A61B 3/0025* (2013.01); *A61B 3/102* (2013.01); *A61B 3/1025* (2013.01); *A61B 3/113* (2013.01); *A61B 3/152* (2013.01)

(58) Field of Classification Search
CPC ........... A61B 3/152; A61B 3/14; A61B 3/102; A61B 3/12; A61B 3/0025
USPC .................................................. 351/200–246
See application file for complete search history.

(56) References Cited

U.S. PATENT DOCUMENTS

| | | | |
|---|---|---|---|
| 9,109,870 | B2 | 8/2015 | Bajraszewski et al. |
| 9,310,187 | B2 | 4/2016 | Bajraszewski et al. |
| 9,585,555 | B2 | 3/2017 | Dziubak et al. |

(Continued)

FOREIGN PATENT DOCUMENTS

| | | |
|---|---|---|
| JP | 2013-154189 A | 8/2013 |
| WO | 2015/189174 A2 | 12/2015 |

OTHER PUBLICATIONS

Aug. 9, 2017 European Search Report in European Patent Application No. 17160000.0.

*Primary Examiner* — Mohammed Hasan
(74) *Attorney, Agent, or Firm* — Fitzpatrick, Cella, Harper & Scinto

(57) ABSTRACT

The ophthalmologic apparatus includes: a scanning unit that scans a fundus of an eye to be inspected with measurement light; a selecting unit that selects one imaging mode out of a first imaging mode and a second imaging mode which is different from the first imaging mode; an acquiring unit that acquires information which indicates a movement amount of the eye to be inspected, based on a plurality of planar images of the fundus; and a correcting unit that corrects a scanning position of the measurement light in an initial scan which is executed after the information indicating the movement amount has been acquired, in the first imaging mode, and corrects the scanning position of the measurement light in an initial scan included in an initial scanning group which is executed after the information indicating the movement amount has been acquired, in the second imaging mode.

8 Claims, 5 Drawing Sheets

(56) References Cited

U.S. PATENT DOCUMENTS

| | | | | |
|---|---|---|---|---|
| 2012/0253183 | A1* | 10/2012 | Muto | G06T 19/00 600/425 |
| 2013/0258349 | A1 | 10/2013 | Makihira et al. | |
| 2014/0063452 | A1* | 3/2014 | Aoki | A61B 3/0091 351/206 |
| 2014/0063460 | A1* | 3/2014 | Borycki | A61B 3/102 351/208 |
| 2014/0276025 | A1 | 9/2014 | Durbin et al. | |
| 2015/0062532 | A1 | 3/2015 | Sharma et al. | |
| 2015/0297077 | A1 | 10/2015 | Shimozato et al. | |
| 2017/0027443 | A1 | 2/2017 | Sakagawa et al. | |

* cited by examiner

OPHTHALMOLOGIC APPARATUS AND IMAGING METHOD

BACKGROUND OF THE INVENTION

Field of the Invention

The present invention relates to an ophthalmologic apparatus and an imaging method.

Description of the Related Art

Optical coherence tomography (hereinafter referred to as OCT) becomes commercially practical as a method for non-destructively and non-invasively acquiring a tomographic image of a measurement object such as a living body. The OCT can acquire information concerning tomographic images of the retina in the fundus of an eye to be inspected particularly in the ophthalmologic field, and is widely used in an ophthalmologic diagnosis of the retina, and the like.

In the OCT, light reflected from the measurement object interferes with reference light, the time dependency or wave number dependency of the intensity of the light that has interfered is analyzed, and thereby information concerning the tomographic images can be obtained. As for an optical coherence tomographic imaging apparatus (hereinafter referred to as an OCT apparatus) using such an OCT, a time domain OCT apparatus is known which obtains depth information of the measurement object by changing the position of a reference mirror. In addition, a spectral domain OCT (SD-OCT: Spectral Domain Optical Coherence Tomography) apparatus using a broadband light source is also known. Furthermore, a wavelength swept-OCT (SS-OCT: Swept Source Optical Coherence Tomography) apparatus is also known which uses a wavelength variable light source device that can change an oscillation wavelength as a light source. Incidentally, the SD-OCT and SS-OCT are collectively referred to as Fourier domain OCT (FD-OCT: Fourier Domain Optical Coherence Tomography).

In recent years, an angiography using this FD-OCT has been proposed and is called as OCT Angiography (hereinafter referred to as OCTA).

The fluorescence contrast imaging which is a common angiography in modern clinical medical care requires injection of a fluorescent dye (for instance, fluorescein or indocyanine green) into the body, and two-dimensionally displays a vessel which is a pathway of the fluorescent dye. However, there are side effects on the contrast medium, there are also cases where the contrast medium causes nausea, rash and cough and rarely causes shock symptoms, and thus fluorescence imaging involves a risk. On the other hand, the OCTA enables non-invasive angiography, and can display a vascular network three-dimensionally. Furthermore, the OCTA can visualize microvessels of the fundus when being used in the ophthalmologic diagnosis or the like, and accordingly is attracting attention.

Here, the OCTA is a technique of specifying a vessel region by repeatedly (a plurality of times) scanning the same site of a measurement object and extracting a difference between the signals that are acquired by each scan. Incidentally, in the present specification, it is called as cluster (group) scanning to scan the same site of the measurement object a plurality of times, which corresponds to the same scanning line, and a group of a plurality of scans that are included in the cluster scanning is referred to as a scanning group. On the other hand, it is called as single (single) scanning to scan the same site of the measurement object only once, which corresponds to the same scanning line.

In the OCTA and general OCT, it is desired that the apparatus tracks the movement of the measurement object (tracking) and corrects the scanning position (hereinafter referred to as tracking operation), when two-dimensionally scanning the surface of the measurement object. Regarding this, in the field of the OCT, it is known that the apparatus performs the tracking operation for each main scanning (B-scan) in two-dimensional scanning, with respect to the movement of the measurement object by reason of a fixation failure or the like of an eye to be inspected which is the measurement object (Japanese Patent Application Laid-Open No. 2013-154189).

However, in the OCTA, the time period which is needed for one cluster scanning is limited, and there is a case where it is not appropriate to apply the above tracking operation for each main scanning as it is in the general OCT. In other words, in the OCT apparatus, there is a case where the timing at which the apparatus should correct the scanning position in the tracking operation varies depending on an imaging mode such as an imaging mode using the OCTA (OCTA mode) or an imaging mode using the general OCT (OCT mode).

SUMMARY OF THE INVENTION

With respect to the above described problems, the present invention provides an ophthalmologic apparatus and an imaging method that correct a scanning position in a tracking operation for each imaging mode at an appropriate timing.

According to one embodiment of the present invention, there is provided an ophthalmologic apparatus including: a scanning unit that scans a fundus of an eye to be inspected with measurement light; a selecting unit that selects one imaging mode out of a first imaging mode and a second imaging mode which is different from the first imaging mode; an acquiring unit that acquires information which indicates a movement amount of the eye to be inspected, based on a plurality of planar images of the fundus; and a correcting unit that corrects a scanning position of the measurement light in an initial scan which is executed after the information indicating the movement amount has been acquired, in a case where the first imaging mode has been selected, and corrects the scanning position of the measurement light in an initial scan included in an initial scanning group which is executed after the information indicating the movement amount has been acquired, in a case where the second imaging mode has been selected.

According to another embodiment of the present invention, there is provided an imaging method for imaging a fundus of an eye to be inspected including: scanning the fundus of the eye to be inspected with measurement light, by a scanning unit; selecting one imaging mode out of a first imaging mode and a second imaging mode which is different from the first imaging mode, by an imaging mode selecting unit; and acquiring information which indicates a movement amount of the eye to be inspected, based on a plurality of planar images of the fundus, by an acquiring unit; correcting a scanning position of the measurement light in an initial scan which is executed after the information indicating the movement amount has been acquired, in a case where the first imaging mode has been selected, by a correcting unit; and correcting the scanning position of the measurement light in an initial scan included in an initial scanning group which is executed after the information indicating the movement amount has been acquired, in a case where the second imaging mode has been selected, by the correcting unit.

Further features of the present invention will become apparent from the following description of exemplary embodiments with reference to the attached drawings.

DESCRIPTION OF THE EMBODIMENTS

Figure 1:
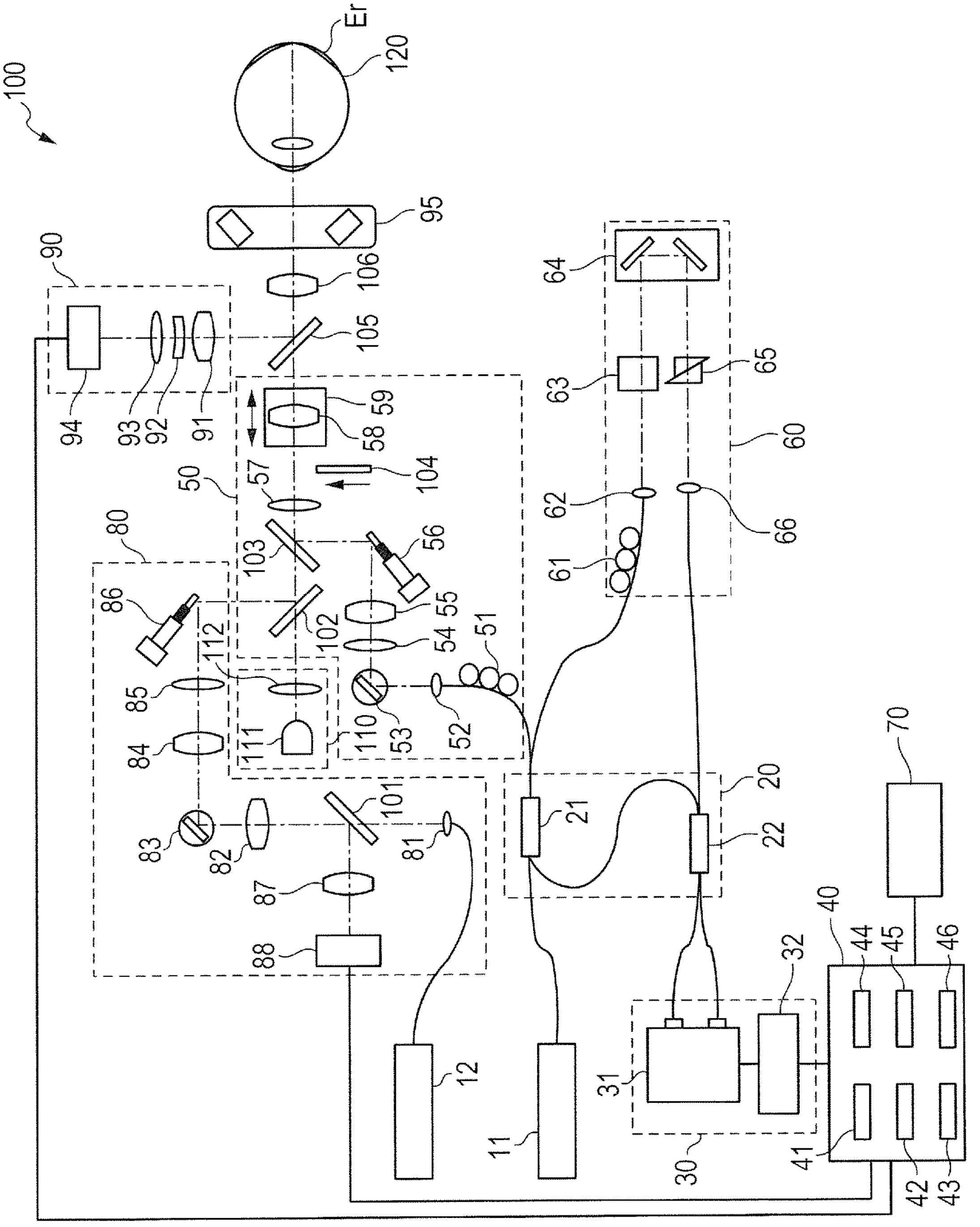
FIG. 1 is a schematic view of the whole configuration of an imaging apparatus in one embodiment of the present invention.

Preferred embodiments of the present invention will now be described in detail in accordance with the accompanying drawings.

However, the dimension, material, shape, relative position of a component, and the like, which will be described in the following embodiments, are arbitrary, and can be changed according to the configuration of the apparatus to which the present invention is applied, or to various conditions. In addition, in order to denote identical or functionally similar elements in the drawings, the same reference numerals are used among the drawings. Incidentally, in the present specification, the same place, the same scanning position and the same scanning line are not intended to mean the place or the like, which strictly coincides with itself, but are intended to mean the place that allows a deviation within a predetermined range, from a place which is desired to be imaged. In addition, the deviation to be allowed includes also a deviation which is intentionally caused in the case or the like where a cluster scan is performed in order to reduce a noise in a tomogram image, in addition to a deviation which is caused by an error originating in an operation of the apparatus and fine movement originating in a measurement object.

[Configuration of Whole Imaging Apparatus]

An ophthalmologic apparatus according to one embodiment of the present invention will be described in detail below with reference to the drawings. FIG. 1 schematically illustrates a configuration example of an imaging apparatus (OCT apparatus) 100 using an optical coherence tomography method, which is an example of an ophthalmologic apparatus according to the present embodiment. The OCT apparatus 100 includes, for instance, an imaging system which uses SD-OCT or SS-OCT. In the present embodiment, a configuration is shown in the case where the OCT apparatus 100 includes the imaging system using the SS-OCT. Incidentally, in the present embodiment, a body 120 to be inspected (measurement object) is a human eye, but the measurement object which is measured by the present invention is not limited to the human eye.

The OCT apparatus 100 is provided with: a wavelength sweeping light source 11 which sweeps a frequency of light to be emitted; an OCT coherence unit 20 in which interference light occurs; a detecting unit 30 which detects the interference light; and a computer 40 which acquires information on the fundus Er of the body 120 to be inspected (eye to be inspected), based on the interference light. Furthermore, the OCT apparatus 100 is provided with: a measuring arm 50; a reference arm 60; and a display unit 70. In addition, the OCT apparatus 100 is provided with: an SLO light source 12 for a scanning type ophthalmoscope (Scanning Laser Ophthalmoscope: hereinafter referred to as SLO); an SLO optical system 80 for obtaining light reflected from the fundus Er; and an anterior segment imaging optical system 90. Incidentally, the display unit 70 may be a display provided in the OCT apparatus 100, or may also be a separate display which is connected to the OCT apparatus 100.

<Configuration of OCT Measuring System>

An OCT measuring system will be described below which acquires information concerning a tomographic image of the fundus Er of the body 120 to be inspected, based on returned light of the measurement light from the fundus and reference light. The OCT measuring system includes the wavelength sweeping light source 11, the OCT coherence unit 20, the measuring arm 50, the reference arm 60 and the detecting unit 30.

The OCT coherence unit 20 is provided with couplers 21 and 22. Firstly, the coupler 21 divides the light emitted from the wavelength sweeping light source 11 into the measurement light which irradiates the fundus Er and the reference light. In the present embodiment, the division ratio of the light by the coupler 21 is approximately 2:8, and is set to be measurement light:reference light=2:8.

The measurement light irradiates the fundus Er of the body 120 to be inspected by way of the measuring arm 50. More specifically, a polarization state of the irradiation light incident on the measuring arm 50 is adjusted by a polarization controller 51, and then the irradiation light is emitted from the collimator 52 as spatial light. After that, the irradiation light passes through an X-scanning scanner 53, lenses 54 and 55, a Y-scanning scanner 56, a dichroic mirror 103, a lens 57, a focus lens 58 fixed to a focus stage 59, a dichroic mirror 105 and an objective lens 106. The irradiation light which has been emitted from the collimator 52 as spatial light passes through the optical path, and irradiates the fundus Er of the body 120 to be inspected.

Incidentally, the X-scanning scanner 53 and the Y-scanning scanner 56 are structured by using a galvanometer mirror or the like, for instance. The X-scanning scanner 53 and the Y-scanning scanner 56 constitute a scanning unit (scanning means) that has a function of scanning the fundus Er with the irradiation light. The scanning unit can change the position of the fundus Er, which the measurement light irradiates. The focus stage 59 can move in a direction of the optical axis along an arrow illustrated in the figure, and can adjust the focal point of the measurement light onto the fundus Er by moving the focus lens 58. In addition, the dichroic mirror 103 has characteristics of reflecting light that has a wavelength of 1000 nm to 1100 nm, and transmitting the other light therethrough. Furthermore, the dichroic mirror 105 has characteristics of reflecting light having a wavelength of 820 nm to 920 nm, and transmitting the other light therethrough.

Then, a back-scattered light (reflected light) from the fundus Er traces the above described optical path again, and is emitted from the measuring arm 50. Then, the emitted light passes through a coupler 21, and is incident on a coupler 22. In the coupler 21, 80% of returned light (reflected light) from the fundus Er is guided to the coupler 22 according to the previously described division ratio.

On the other hand, the reference light passes through the reference arm 60, and is incident on the coupler 22. More specifically, a polarization state of the reference light incident on the reference arm 60 is adjusted by the polarization controller 61, and then the resultant light is emitted from the collimator 62 as spatial light. After that, the reference light passes through a dispersion compensating glass 63, an optical path length adjusting optical system 64, and a dispersion adjusting prism pair 65, is incident on an optical fiber through the collimator 66, is emitted from the reference arm 60, and is incident on the coupler 22.

Here, the dispersion compensating glass 63 and the dispersion adjusting prism pair 65 can adjust the dispersion of the reference light. Because of this, the dispersion of the reference light can be adjusted by using the dispersion compensating glass 63 and the dispersion adjusting prism pair 65 so that the dispersion of the reference light corresponds to the dispersion of the reflected light which passes through the measuring arm 50. In addition, the optical path length adjusting optical system 64 can move in a direction of getting closer to or getting away from the collimators 62 and 66, and can adjust the optical path length of the reference arm 60. For this reason, the optical path length adjusting optical system 64 can adjust the optical path length of the reference arm 60 according to a length of the optical path through which the measurement light irradiated to the fundus Er of the body 120 to be inspected passes.

The reflected light from the body 120 to be inspected, which has passed through the measuring arm 50, and the light which has passed through the reference arm 60 interfere with each other in the coupler 22. Two branched interference lights are emitted from the coupler 22 into the two optical fibers, and are incident on the detecting unit 30. Then, the detecting unit 30 detects the incident interference light. The detecting unit 30 is provided with a differential detector 31 and an A/D converter 32. Firstly, in the detecting unit 30, the differential detector 31 detects the two interference lights that have been immediately branched after the interference light has occurred in the coupler 22, by the differential detector 31. Here, the two interference lights which are incident on the differential detector 31 are adjusted so that the phases of interference signal components are mutually inverted, and the differential detector 31 detects differentials between the two interference lights and thereby can detect the interference signal component at an adequate SN ratio.

Then, the differential detector 31 sends an interference signal (OCT coherence signal) which has been converted into an electric signal, to the A/D converter 32, and the A/D converter 32 receives the OCT coherence signal and converts the interference signal into a digital signal. Here, in the OCT apparatus illustrated in FIG. 1, the A/D converter 32 samples the OCT coherence signal at equal light-frequency (equal wave number) intervals, based on a k clock signal that is generated by an unillustrated k clock generating unit which is incorporated in the wavelength sweeping light source 11, and converts the sampled interference signal into the digital signal. The A/D converter 32 sends the OCT coherence signal which has been converted into the digital signal, to the computer 40.

The above process is a process of acquiring information concerning the tomograph at one certain point of the body 120 to be inspected, and a method for acquiring the information concerning the tomograph in a depth direction of the body to be inspected in this way is called as an A-scan. In addition, such an operation is called as a B-scan as to scan the body 120 to be inspected in a direction orthogonal to the A scan for acquiring information concerning the tomograph of the body 120 to be inspected, in other words, in a scanning direction for acquiring the information concerning the two-dimensional image. Furthermore, such an operation is called as a C-scan as to scan the body 120 to be inspected in a direction orthogonal to both of the scanning directions of the A-scan and the B-scan. In the case where the OCT apparatus subjects a plane of the fundus of the body 120 to be inspected to two-dimensional raster scanning, at the time when acquiring information on a three-dimensional tomographic image, in particular, a direction in which scanning is performed at high speed (main scanning direction) is called as a B-scan direction. In addition, a direction of scanning at low speed (sub-scanning direction) is called as a C-scan direction, in which the OCT apparatus scans the plane in such a way as to arrange the B-scans in its orthogonal direction.

In the OCT measuring system, the OCT apparatus can obtain the information concerning the two-dimensional tomographic image by performing the A-scan and the B-scan, and can obtain the information concerning the three-dimensional tomographic image by performing the A-scan, the B-scan and the C-scan. The B-scan and the C-scan are performed by the above described X-scanning scanner 53 and Y-scanning scanner 56.

Incidentally, the X-scanning scanner 53 and the Y-scanning scanner 56 are respectively formed of mirrors of which the rotation axes are orthogonal to each other. The X-scanning scanner 53 performs scanning in the X-axis direction, and the Y-scanning scanner 56 performs scanning in the Y-axis direction. The respective directions in the X-axis direction and the Y-axis direction are directions which are perpendicular to the eye axis direction of the eyeball and are perpendicular to each other. The line scanning direction as in the B-scan and the C-scan may not coincide with the X-axis direction or the Y-axis direction. Because of this, the line scanning directions of the B-scan and the C-scan can be appropriately determined according to the two-dimensional tomographic image or the three-dimensional tomographic image which are desired to be picked up.

<Configuration of SLO Measuring System>

An SLO measuring system will be described below which irradiates the fundus Er of the body 120 to be inspected with light emitted from the SLO light source 12, and acquires information concerning an image of the surface of the fundus from the reflected light from the fundus Er. The SLO measuring system includes the SLO light source 12, the SLO optical system 80, and a part of the measuring arm 50.

The light that has been emitted from the SLO light source 12 irradiates the fundus Er through the SLO optical system 80. More specifically, the light that has been incident on the SLO optical system 80 is emitted from the collimator 81 to the space as parallel light. After that, the light passes through a perforated portion of a perforated mirror 101, and reaches the dichroic mirror 102 through the lens 82, the X-scanning scanner 83, the lenses 84 and 85, and the Y-scanning scanner 86. Here, the X-scanning scanner 83 and the Y-scanning scanner 86 are configured by using a galvanometer mirror, for instance, and constitute a scanning unit (scanning means) for the SLO measuring system. Incidentally, the X-scanning scanner 83 and the Y-scanning scanner 86 are one example of the scanning unit for the SLO measuring system, and a configuration is also acceptable which uses the X-scanning scanner 53 and the Y-scanning scanner 56 for the OCT measuring system as a common XY-scanning scanner of the OCT measuring system and the SLO measuring system. The dichroic mirror 102 has characteristics of reflecting light having a wavelength of 760 nm to 800 nm, and transmitting the other light therethrough.

The light which has been reflected by the dichroic mirror 102 passes through the same optical path as that in the OCT measuring system, in other words, passes through the dichroic mirror 103, the lens 57, the focus lens 58 fixed to the focus stage 59, the dichroic mirror 105 and the objective lens 106. The light that has been emitted from the SLO light source 12 and has been reflected by the dichroic mirror 102 passes through these optical paths, and reaches the fundus Er of the body 120 to be inspected.

Measurement light that has been emitted from the SLO light source 12 and has irradiated the fundus Er is reflected and scattered by the fundus Er, traces the above described optical paths, and reaches the perforated mirror 101. The light that has been reflected by the perforated mirror 101 is incident on an avalanche photodiode (hereinafter referred to as APD) 88 through a lens 87. The APD 88 receives the incident light, converts the light into an electric signal, and sends the electric signal to the computer 40.

Here, the position of the perforated mirror 101 is conjugate with the pupil position of the eye to be inspected which is the body 120 to be inspected, and the light that has passed the peripheral portion of the pupil, out of lights that have been generated by the measurement light that has irradiated the fundus Er and has been reflected and scattered, is reflected by the perforated mirror 101.

<Configuration of Anterior Segment Measuring System>

The configuration of the anterior segment measuring system for imaging the anterior segment of the body 120 to be inspected will be described below. The anterior segment measuring system includes an illumination light source 95, and an anterior segment imaging optical system 90.

The anterior segment imaging optical system 90 irradiates the anterior segment of the body 120 to be inspected with illumination light having a wavelength of 860 nm, which has been emitted from an illumination light source 95 formed of an LED. The light reflected by the anterior segment reaches the dichroic mirror 105 through the objective lens 106. As described above, the dichroic mirror 105 has characteristics of reflecting light having a wavelength of 820 nm to 920 nm, and transmitting the other light therethrough. The light reflected by the dichroic mirror 105 is incident on the anterior segment camera 94 through the lenses 91, 92 and 93. The anterior segment camera 94 receives the incident light, converts the light into an electric signal, and sends the electric signal to the computer 40.

<Internal Fixation Lamp 110>

The internal fixation lamp 110 for indicating a fixation target for promoting the fixation of the eye to be inspected which is the body 120 to be inspected will be described below.

The internal fixation lamp 110 is provided with a display unit 111 for the internal fixation lamp and a lens 112. As for the display unit 111 for the internal fixation lamp, a device is used in which a plurality of light-emitting diodes (LD) are arranged in a matrix form. The lighting position of the light-emitting diode can be changed by an unillustrated input unit or the computer 40, according to a site which is desired to be imaged. The light emitted from the display unit 111 for the internal fixation lamp is guided to the eye to be inspected, through the lens 112. The light which is emitted from the display unit 111 for the internal fixation lamp has a wavelength of 520 nm, and is displayed with a set desired pattern.

<Computer 40>

The computer 40 subjects an interference signal or the like, which has been converted into a digital signal, to signal processing, and generates an optical coherence tomogram image, a blood flow information tomogram image, an SLO fundus image, an anterior segment image and the like, and calculates the fundus movement amount and the like. The computer 40 includes a control unit 41, a storage unit 42, an imaging mode selecting unit 43, a changing unit 44, an acquiring unit 45, and a correcting unit 46.

The control unit 41 (storage control unit) controls the scanning units of the OCT measuring system and the SLO measuring system, and controls image processing of an acquired image, information to be stored in the storage unit 42, and the like. The storage unit 42 (storage means) is configured by using arbitrary storage unit such as a memory or an optical disk, and can memorize and store various information therein. The imaging mode selecting unit 43 (imaging mode selecting means) can select the imaging mode, based on the input by an inspector, a past inspection and the like. The changing unit 44 (changing means) can change a scanning range of the measurement light by the OCT measuring system or the like, the number of times of scans in the scanning group, and a scanning resolution of the measurement light, based on the input by the inspector, the past inspection and the like. The acquiring unit 45 (acquiring means) can acquire the movement amount of the fundus Er, based on the information sent from the SLO measuring system or the like. The correcting unit 46 (correcting means) can correct the position which the X-scanning scanner 53 and the Y-scanning scanner 56 irradiate with the measurement light, based on the movement amount of the fundus Er.

Specific processing contents will be described later which are performed by these components contained in the computer 40. The computer 40 sends the information on the fundus Er and the anterior segment obtained by calculation, to the display unit 70, and the display unit 70 displays these information.

The computer 40 can be formed of a general computer, and each of the above described components provided in the computer can be achieved by a program which is executed by a processor such as a CPU and an MPU of the computer. In addition, the computer 40 may be a dedicated computer, and each of the above described components may be configured by using a circuit (for instance, ASIC) which achieves one or more functions.

Incidentally, the computer 40 takes a difference between the interference signals, based on the two interference lights that have been detected by the differential detector 31 in the OCT measuring system and have phases of the interference signal components, either of which is inverted from the other, thereby detects the interference component of the interference signal, and can reduce a noise originating in a non-interference component of the interference signal. For this reason, by detecting the differentials, the computer 40 can improve a signal-to-noise ratio (S/N ratio) of information on the fundus based on the interference signal.

Here, the OCT measuring system and the computer 40 are included in the OCT imaging system (first generating unit)

that generates a tomogram image of the fundus, based on the reference light and the returned light from the fundus of the measurement light. Furthermore, the SLO measuring system and the computer 40 are included in the SLO imaging system (second generating unit) that generates a planar image of the fundus, which is different from the tomogram image. Incidentally, the OCT imaging system and the SLO imaging system may be configured so as to have separate calculation units (processor), respectively.

Incidentally, the OCT apparatus 100 in the present embodiment is configured so that the shutter 104 can be inserted between the lens 57 and the focus stage 59 in the measuring arm 50. The control unit 41 moves the shutter 104 in the illustrated arrow direction, inserts the shutter 104 onto the optical axis between the lens 57 and the focus stage 59, performs imaging, and thereby can acquire background data concerning the OCT imaging system and the SLO imaging system. Here, the background data means data which contains a noise inherent in the configuration of each of the imaging systems. Because of this, the OCT apparatus 100 can reduce the noise for the information of the body 120 to be inspected, which originates in the configuration of the imaging system, by taking a difference between the background data and the information obtained by imaging the body 120 to be inspected.

[Setting of Scan Area]

Figure 2:
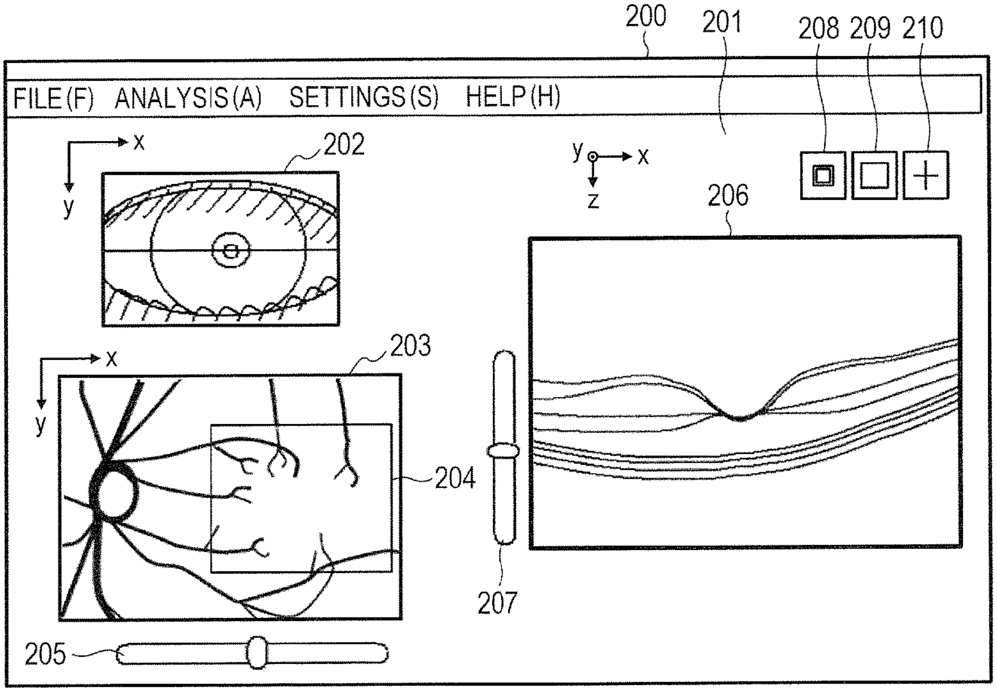
FIG. 2 is an explanatory view of an imaged screen in one embodiment.

FIG. 2 illustrates one example of an imaged screen 200 that is displayed on a display unit 70 at the time of imaging. The anterior segment image 202, the SLO fundus image 203, and the optical coherence tomogram image 206 which have been obtained by calculation in the computer are displayed on the display area 201 which is one example of the display area.

Firstly, the inspector selects a scan mode. Specifically, the inspector selects any one of an OCTA scan icon 208, a volume scan icon 209 and a cross scan icon 210. These scan modes will be described later. There may be various scan modes such as a radial scan, a circle scan, a multi-cross scan, and a single scan, other than the above scan modes. Among them, an imaging mode in the case where the OCTA scan icon 208 has been selected shall be defined as an OCTA mode, and an imaging mode in the case where the other icons have been selected shall be defined as an OCT mode. The imaging mode selecting unit 43 of the computer can select the imaging mode, based on the scan mode which has been selected by the inspector. For instance, the imaging mode selecting unit 43 can select the OCTA mode, when the OCTA scan icon has been selected, and select the OCT mode, when an icon other than the OCTA scan icon has been selected. On the other hand, the imaging mode selecting unit 43 may select the imaging mode for the body 120 to be inspected, from the past inspection and the like. For instance, when the body 120 to be inspected was imaged in the OCTA mode in the past, the imaging mode selecting unit 43 may automatically select the OCTA mode.

Next, the inspector or the computer 40 aligns each of the optical systems of the OCT apparatus 100 in the optical axis direction of the measurement light with respect to the body 120 to be inspected, based on the anterior segment image 202.

Next, the inspector moves the focus stage 59 by using a focus adjusting bar 205 and adjusts the focus so that the SLO fundus image 203 becomes optimum. Alternatively, the computer 40 may adjust the focus by automatically moving the focus stage 59, based on the SLO fundus image 203.

Next, the inspector sets the scan area. The inspector can designate and set the scan area by a guide 204 that is displayed on the SLO fundus image 203. The guide can be set to an arbitrary size, shape and position. The computer 40 displays an arbitrary tomogram image of the scan area that has been designated by the guide 204, as the optical coherence tomogram image 206. Here, the changing unit 44 of the computer 40 can change the scan area (scan range of measurement light), based on the setting by the inspector. The scan area may be automatically set by the changing unit 44 of the computer 40, based on arbitrary information such as the previously set scan area, a lesion site of the body 120 to be inspected, the site of an inspection object in the past and the like.

Finally, the inspector adjusts the gate by using the gate adjustment bar 207 so that the optical coherence tomogram image 206 becomes optimum. Here, the gate adjustment means an operation of adjusting the optical path length in the reference arm 60 by using the optical path length adjusting optical system 64, and thereby, the inspector can adjust the imaging position in the depth direction of the body 120 to be inspected, by the OCT measuring system. Incidentally, the computer 40 may automatically adjust the gate, based on the optical coherence tomogram image 206.

[Scan Pattern in OCTA Mode]

Figure 3A:
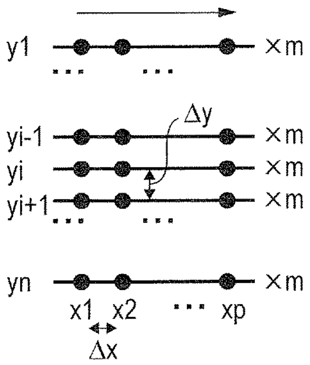
FIG. 3A is an explanatory view of scans in one embodiment.

Next, the scan mode will be described with reference to FIGS. 3A to 3C. FIG. 3A illustrates an example of a scan pattern in the case where the OCTA scan icon 208 has been selected, in other words, the scan pattern in the OCTA mode. Here, the OCTA mode is an imaging mode in which the OCT apparatus acquires blood flow information on the body 120 to be inspected by using OCTA, and in the OCTA mode, the OCT apparatus can image the OCTA image for specifying the blood flow region of the body 120 to be inspected, based on the acquired blood flow information. In the OCTA mode, the OCT apparatus can generate the OCTA image, based on a plurality of interference signals based on the reference light and the returned lights from the fundus Er of the measurement light, which have been obtained by a plurality of times of scans which are contained in the scanning group. Incidentally, in the following description, the X position indicates a position in the B-scan direction, and the Y position indicates a position in the C-scan direction.

In the OCTA, the time change of the OCT coherence signal due to the blood flow is measured, and accordingly it is necessary to measure the interference signals at a plurality of times on the same place (same scanning position) of the body 120 to be inspected. In the present embodiment, the OCT apparatus 100 repeats the B-scan at the same place m times ($m \geq 2$), and performs the C-scan that moves to n portions of the Y positions (scanning positions). Specifically, the OCT apparatus 100 repeats the B-scan m times for each of n portions of Y positions y1 to yn, on the planar surface of the fundus.

When m is large, the number of measurements at the same place increases, and accordingly the detection accuracy of the blood flow is enhanced. On the other hand, the time period (scanning time period) which is required for scanning becomes longer, and accordingly there arise a problem that motion artifacts are generated in the image due to the movement of the eye during scanning (fixation fine movement), and a problem that a burden on a person to be inspected increases. In the present embodiment, m=3 is set in consideration of the balance between both the problems. Incidentally, m may be freely changed according to the A-scan speed of the OCT apparatus 100 and the movement amount of the eye of the body 120 to be inspected. Incidentally, m can be changed through the changing unit 44 of the computer 40, based on the inspector's input or the like.

In FIG. 3A, p represents the number of sampling for the A-scan in one B-scan. Specifically, the planar image size is determined by p×n. If the value of p×n is large, a wide range can be scanned, but the scanning time period becomes long as long as the measurement pitches are equal, and accordingly there arise the above described problems of the motion artifacts and the burden of the patient.

In FIG. 3A, Δx is a space (x pitch) between adjacent X positions, and Δy is a space (y pitch) between adjacent Y positions. In the present embodiment, the x pitch is determined as ½ of the beam spot diameter of the irradiation light at the fundus Er, and is set at 10 μm. In addition, Δy is set at 10 μm similarly to Δx. Incidentally, even if each pitch is made smaller than ½ of the beam spot diameter on the fundus, an effect of enhancing the definition of the image to be generated is small. In addition, in order to shorten the scanning time period, Δy may be set larger than 10 μm, but may be set in such a range as not to exceed the beam spot diameter which is 20 μm. As for the x pitch and the y pitch, when the beam spot diameter of the fundus is increased, the definition of the image decreases, but a wide range of images can be acquired with a small data capacity. The x pitch and the y pitch may be freely changed according to clinical demands. The scanning resolution of the measurement light originating in the measurement pitch can be changed, based on the input or the like by the inspector through the changing unit 44 of the computer 40.

[Scan Pattern in OCT Mode]

Figure 3B:
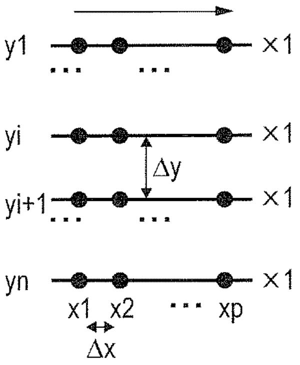
FIG. 3B is an explanatory view of scans in one embodiment.

FIG. 3B illustrates one example of a scan pattern in the case where the volume scan icon 209 has been selected, in other words, the scan pattern of a volume scan in the OCT mode. The OCT mode is an imaging mode that acquires the information concerning the tomographic image of the body 120 to be inspected other than the OCTA image, and in the OCT mode, the OCT apparatus can image the tomogram image of the body 120 to be inspected, based on the acquired information.

The volume scan is a scan that acquires three-dimensional data of the fundus Er. The scan pattern of the volume scan is similar to the scan pattern of the OCTA scan, but the number of times of the B-scans at each yi may be one, in other words, may be m=1. FIG. 3B illustrates the scan pattern of the volume scan in the case of m=1. In addition, the x pitch and the y pitch may be greatly different. When it is a purpose to observe the optical coherence tomographic image obtained by the B-scan in the X-direction, in particular, it is desirable to decrease the x pitch and to increase the y pitch. As a result, the OCT apparatus can acquire a fine optical coherence tomogram image in the B-scan direction in a short period of time. In the case where the B-scan at each scanning position yi is performed twice or more, the optical coherence tomogram image obtained at each of the scanning positions yi is subjected to Intensity averaging processing which will be described later, and thereby a high-definition optical coherence tomogram image can be obtained in which an influence of the noise is reduced.

Figure 3C:
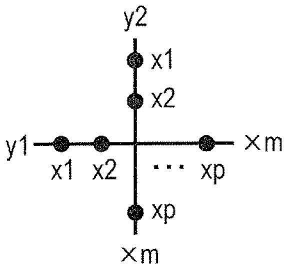
FIG. 3C is an explanatory view of scans in one embodiment.

FIG. 3C illustrates one example of a scan pattern in the case where the cross scan icon 210 has been selected, in other words, the scan pattern of a cross scan in the OCT mode.

The cross scan is a scan that acquires an optical coherence tomographic image of one position in each of the X-direction and the Y-direction on the fundus Er. In the cross scan, the OCT apparatus performs the B-scan of the same site m times in the X-direction, and the B-scan of the same site m times in the Y-direction. Here, the X-direction and the Y-direction do not mean the B-scan direction and the C-scan direction, but simply mean the X-axis direction and the Y-axis direction. In addition, m is an arbitrary integer of 1 or more. Similarly to the case of the volume scan, when m is 2 or more, a high-resolution optical coherence tomogram image can be obtained by the Intensity averaging processing. In the cross scan, the sites to be imaged are only two positions of y1 and y2, and accordingly even when m is increased, the influence on the imaging time period is small. Specifically, when m is set at approximately 50, a very high-definition image can be obtained with an imaging time period which gives a little burden on a person to be inspected. Incidentally, in the present embodiment, the number of sampling of the A-scan included in the B-scan in the X-direction and the number of sampling of the A-scan included in the B-scan in the Y-direction are determined to be the same p, but may be a different number of sampling from each other.

As has been described above, there are various scan patterns other than the above scan patterns, and scan patterns in the OCTA mode and the OCT mode are not limited to the above scanning pattern.

[Signal Processing Procedure]

The procedure of processing the interference signal in the OCT imaging system will be described below. This is a procedure for obtaining information concerning the retinal image, in the case of the OCT mode, and is a procedure for obtaining the blood flow information, in the case of the OCTA mode. In order to generate information on the three-dimensional blood flow by the OCTA, the computer calculates a motion contrast characteristic amount. Here, the motion contrast is defined as a contrast between a flowing tissue (for instance, blood) and a non-flowing tissue, out of tissues of the body to be inspected. In addition, the characteristic amount that expresses the motion contrast is defined as the motion contrast characteristic amount. The motion contrast characteristic amount may be an indicator that represents the change of the luminance value of each pixel between the tomogram images which have been obtained by a plurality of B-scans at the same Y position. In relation to this indicator, there are various methods for determining the motion contrast characteristic amount, and an arbitrary determination method can be used according to the characteristic amount to be an object. In the present embodiment, a variance value is calculated for each pixel of the same position among images of m pieces of frames obtained by m times of the B-scans, and the variance value is determined as the motion contrast characteristic amount.

Figure 4:
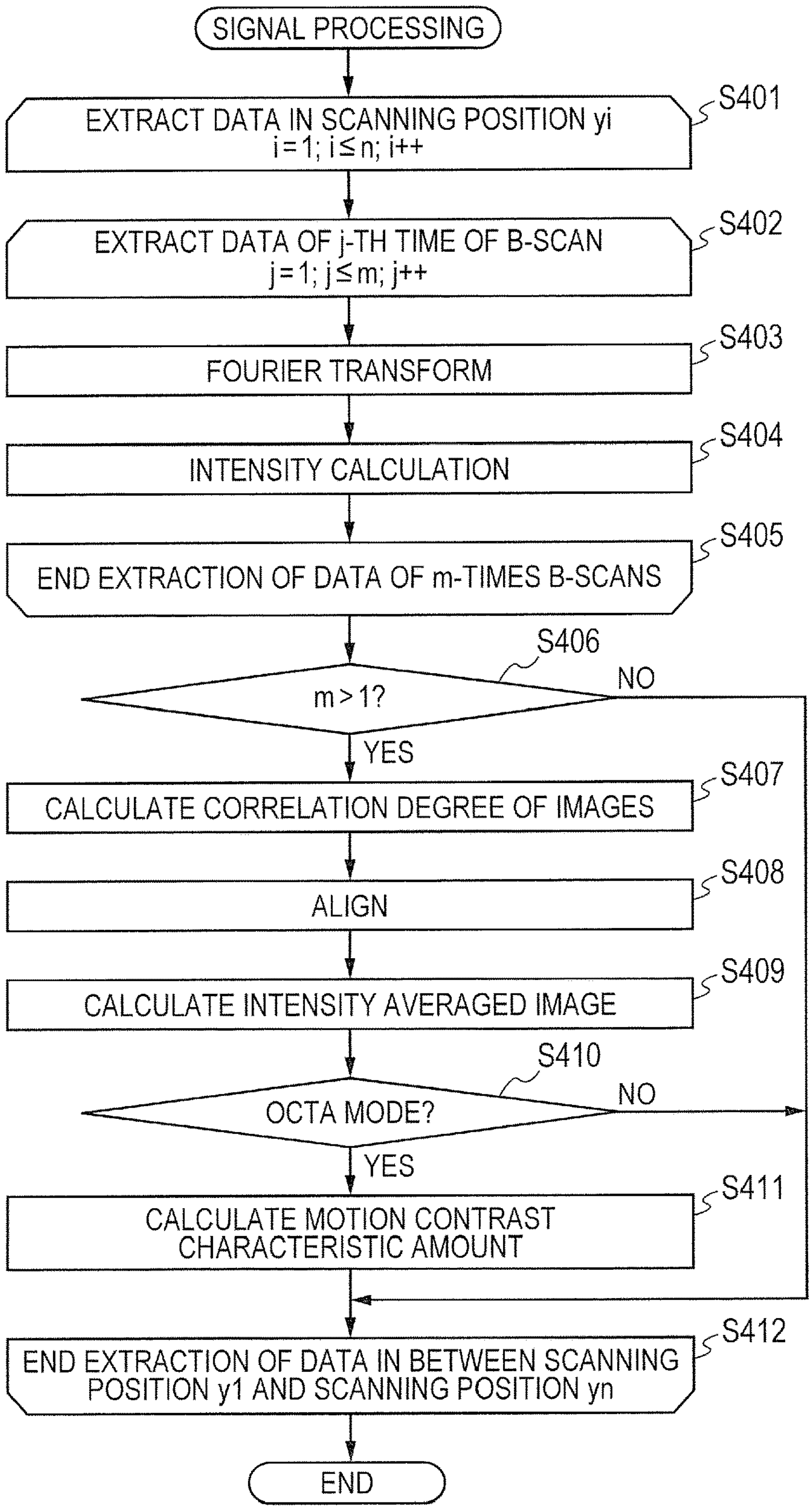
FIG. 4 is an explanatory view of an interference signal processing procedure in one embodiment.

The specific processing procedure of the signal processing of the present embodiment will be described below with reference to FIG. 4. FIG. 4 is a flow from the time when the computer 40 to which the interference signal is input performs the signal processing to the time when the computer 40 outputs the tomogram image or the three-dimensional blood flow information of the retina, as a result.

In a step S401, the control unit 41 of the computer 40 starts the signal processing of the interference signal at the scanning position yi. When the control unit 41 performs the step S401 for the first time, i is 1, which is an index of the scanning position. In the step S401, the control unit 41 compares i with n every time when performing the operations from a step S402 reaching to a step S411, and determines whether or not the i has reached the predetermined number (n). That is, the control unit 41 determines whether or not extraction of the data based on the interference signal obtained by the B-scan has been performed for the predetermined n portions in the Y position.

Specifically, in the step S401, the control unit 41 compares i with n, and increments i by 1 if the i is smaller than n. After having incremented i, the control unit 41 executes the operations from the step S402 reaching to the step S411, then returns the process to the step S401, and compares i with n again. Specifically, when i is less than the predetermined number (n), the processing proceeds to the step S402, and extracts data based on the interference signal that has been obtained by the B-scan at the scanning position yi. When i becomes equal to or larger than n in the step S401, the control unit 41 moves the process to a step S412, and ends the signal processing of the interference signals in between the scanning position y1 and the scanning position yn. In other words, the control unit 41 ends the extraction of the data based on the interference signal in between the scanning position y1 and the scanning position yn, in the step S412.

In the step S402, the control unit 41 starts the signal processing of the interference signal by the j-th time of B-scan at the scanning position yi. When the control unit 41 performs the step S402 at each of the scanning positions yi for the first time, j is 1, which is the index of the B-scan. In the step S402, the control unit 41 compares j with m every time when performing the operation from a step S403 reaching to a step S404, and determines whether or not the j has reached the predetermined number (m). That is, the control unit 41 determines whether or not the Intensity calculation of the interference signals acquired by the B-scan at the scanning position yi has been repeated m times.

Specifically, the control unit 41 compares j to m in the step S402, and increments j by 1 if the j is smaller than m. After having incremented j, the control unit 41 executes the operations from the step S403 reaching the step S404, then returns the process to the step S402, and compares j with m again. Specifically, when j is less than the predetermined number (m), the processing proceeds to the step S403, and repeats the Intensity calculation of the interference signal that has been obtained by the B-scan at the same Y position. When j becomes equal to or larger than m in the step S402, the control unit 41 moves the process to a step S405, and ends the signal processing of each interference signal in between the first time of B-scan and the m-th time of B-scan at the scanning position yi. In other words, the control unit 41 ends the extraction of the data based on the interference signal for m times of scanning at the scanning position yi, in the step S405.

In the step S403, the control unit 41 reads out the interference signal acquired by the j-th time of B-scan from the storage unit 42, and subjects the read-out interference signal to Fourier transform. In the present embodiment, the control unit 41 applies Fast Fourier Transform (FFT) to the read-out interference signal. In the step S404, the control unit 41 calculates an absolute value of a complex signal that is obtained by the Fourier transform which has been executed in the step S403. This value is defined as Intensity.

In the step S405, when the control unit 41 has ended the extraction of the data based on the interference signals corresponding to m times of scanning at the scanning position yi, the process proceeds to a step S406.

In the step S406, the control unit 41 determines whether or not m is a value larger than 1. When m is larger than 1, the process proceeds to a step S407. Here, in the case where m is a natural number, and m is 1 or less, in other words, is 1, the process skips the steps in between the step S407 and the step S411. Incidentally, as for a modified example, the control unit 41 may determine whether or not the imaging mode is a mode of performing the cluster scanning, such as the OCTA mode, in the step S406. In this case, when the imaging mode is the mode of performing the cluster scanning, the process proceeds to the step S407, and when the imaging mode is not a mode of performing the cluster scanning, the process skips the steps in between the step S407 and the step S411.

In the step S407, the control unit 41 calculates a degree of similarity of the images between the Intensity images of m frames (hereinafter referred to as B-scan images of m frames) based on the interference signals obtained by the B-scans at the scanning position yi. Specifically, the control unit 41 selects arbitrary one image out of the B-scan images of the m frames as a template, and calculates a correlation value with the images of the remaining m−1 frames.

In the step S408, the control unit 41 adjusts the positions of each frame between the B-scan images of the m frames at the scanning position yi.

Specifically, the control unit 41 firstly selects arbitrary one image out of the images of the m frames, as a template. The control unit 41 may also calculate the correlation of all combinations in the images of the m frames between each other, determine the sum of correlation coefficients of each of the frames, and select an image of the frame of which the sum of the correlation coefficients becomes largest, as the image of which the frame is selected as the template.

Next, the control unit 41 compares each of the frames with the template, and determines the positional deviation amount (δX, δY and δθ) for each of the frames. Specifically, the control unit 41 calculates Normalized Cross-Correlation (NCC) that is an index which indicates the degree of similarity with each of the frames, while changing the position and angle of the template image. The control unit 41 determines a difference of positions between the image of the frame to be compared and the template image, at the time when the value of the calculated NCC becomes largest, as the positional deviation amount. Incidentally, in the present embodiment, the index indicating the degree of the similarity between the images may be a scale that indicates the degree of the similarity of the features between the image of the frame to be compared and the template image, and can be variously changed to an arbitrary index which indicates the scale.

The control unit 41 applies the position correction to the m−1 frames except the template, according to the determined positional deviation amount (δX, δY and δθ), and thereby aligns the frames.

In the step S409, the control unit 41 averages the Intensity images of the m frames, and generates an Intensity averaged image. Here, the control unit 41 may average the sum of a plurality of interference signals based on the reference light and the returned lights from the fundus Er of the measurement light, which have been obtained by a plurality of times of scans included in the scanning group, and thereby may generate the Intensity averaged image (tomogram image of the fundus).

In a step S410, the control unit 41 determines whether or not the imaging mode is the OCTA mode. When the imaging mode is the OCTA mode, the process proceeds to the step S411. When the imaging mode is not the OCTA mode, in other words, is the OCT mode, the process skips the step S411.

When the imaging mode is the OCTA mode, the control unit 41 calculates the motion contrast characteristic amount, in the step S411. In the present embodiment, as has been described above, the control unit 41 calculates a variance value for each pixel in the same position, among the Intensity images of the m frames, and determines the variance value as the motion contrast characteristic amount.

When having ended the extraction of the data in between the scanning position y1 and the scanning position yn, in the step S412, the control unit 41 ends a signal processing flow. At the time when the control unit 41 has ended the step S412, the Intensity images in the B-scan images at all of the Y positions are obtained. In the case of m>1, in particular, the Intensity average image in the B-scan images at all of the Y positions is obtained. Here, when the imaging mode is the OCT mode, the Intensity average image becomes a desired retinal tomogram image. In addition, when the imaging mode is the OCTA mode, three-dimensional volume data based on the motion contrast characteristic amount in the B-scan images at all of the Y positions are obtained. The three-dimensional volume data becomes desired three-dimensional blood flow information. Incidentally, when the imaging mode is the OCTA mode, the control unit 41 may skip the step S409, and may acquire only the three-dimensional blood flow information.

[Calculation of Fundus Movement Amount]

Figure 5:
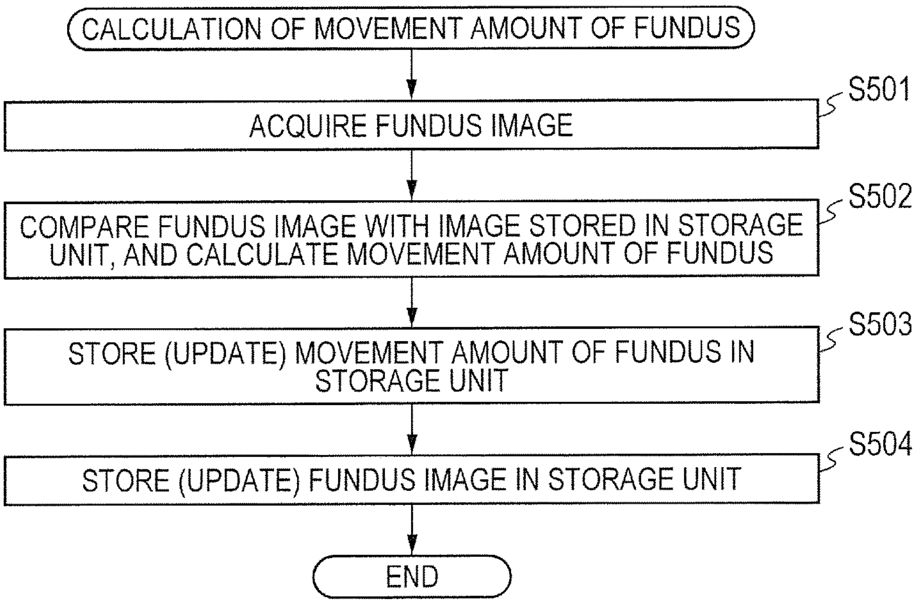
FIG. 5 is an explanatory view of a fundus movement amount calculating procedure in one embodiment.

Next, a method of calculating the deviation between the measurement light irradiation positions (fundus tracking), which is caused by the movement of the eye to be inspected when the fundus portion of the eye to be inspected is irradiated with the measurement light for observing the state of the eye to be inspected, will be described below with reference to the flow chart illustrated in FIG. 5. FIG. 5 illustrates the flow of calculating the fundus movement amount in fundus tracking. Incidentally, according to the flow of calculating the fundus movement amount in the fundus tracking, the OCT apparatus can obtain the movement amount of the fundus Er (fundus movement amount) with the use of the SLO measuring system or the like, which is different from the OCT measuring system. Because of this, according to the flow of calculating the fundus movement amount, the OCT apparatus can be processed asynchronously with the flow of the tracking control with the use of the OCT measuring system, which will be described later.

In a step S501, the control unit 41 of the computer 40 acquires a two-dimensional observation image of the fundus Er of the body 120 to be inspected, using the SLO measuring system. Specifically, the control unit 41 acquires the signal which is input thereinto from an APD 88 and corresponds to the reflected light from the fundus Er. The reflected light from the fundus Er of the eye to be inspected is reflected light of the measurement light continuously scanned two-dimensionally on the fundus by the X-scanning scanner 83 and the Y-scanning scanner 86. Because of this, by combining the signals which are input from the APD 88 and correspond to the reflected light, the control unit 41 can obtain the observation image of the fundus (hereinafter referred to as fundus image).

In a step S502, the acquiring unit 45 (acquiring means) of the computer 40 determines the information that indicates the movement amount of the fundus, by using the two fundus images of the fundus image which has been stored in the storage unit 42 (storage means) before, and the present fundus image. Specifically, the acquiring unit 45 detects displacement amounts (positional deviation amounts) in the two-dimensional (X and Y) directions of the region of interest on the fundus image, and thereby calculates and acquires the movement amounts in the two-dimensional (X and Y) directions of the fundus Er. Furthermore, not only the displacement in the (X and Y) directions, but also the change amount of an angle in a rotation direction may be calculated and included in the movement amount.

In a step S503, the acquiring unit 45 sends the acquired fundus movement amount to the control unit 41 (storage control unit), and the control unit 41 stores the fundus movement amount that the control unit 41 has received, in the storage unit 42. This is because the fundus movement amount is used by the control unit 41 at the time when the scanning position is corrected or the fundus is rescanned in the OCT measuring system, which will be described later. Incidentally, when the fundus movement amount has been already stored in the storage unit 42, the control unit 41 updates the stored fundus movement amount with a newly obtained fundus movement amount. In this case, the storage unit 42 may sequentially store only the new fundus movement amount, and accordingly can reduce the storage capacity necessary for storing the fundus movement amount there. Incidentally, the storage unit 42 may also store a predetermined number of past fundus movement amounts.

In a step S504, the control unit 41 stores the acquired fundus image in the storage unit 42, in order to use the fundus image in the next calculation of the movement amount. Incidentally, when the previous fundus image has been stored in the storage unit 42, the control unit 41 updates the fundus image with a newly acquired fundus image. In this case, the storage unit 42 may sequentially store only the new fundus image, and accordingly can reduce the storage capacity necessary for storing the fundus image there. Incidentally, the storage unit 42 may store a predetermined number of the past fundus images.

The acquiring unit 45 can calculate and acquire the fundus movement amount according to the above described flow, every time when the fundus is two-dimensionally scanned by the X-scanning scanner 83 and the Y-scanning scanner 86. In relation to the calculation, the control unit 41 can update the fundus movement amount that has been stored in the storage unit 42, every time when the acquiring unit 45 acquires the fundus movement amount.

Incidentally, in the present embodiment, the acquiring unit 45 calculates the fundus movement amount by using the fundus image obtained by a point scanning type SLO, but may calculate the fundus movement amount by using another method. For instance, the OCT apparatus may calculate the fundus movement amount by using a two-dimensional fundus image that has been obtained by combining infrared light which can irradiate the fundus in a wide range, with an infrared CCD. In addition, the OCT apparatus may also project an arbitrary pattern that is formed by the light source, onto the fundus, and calculate the fundus movement amount by using the reflected light.

[Correction of Scanning Position]

Next, the correction of the scanning position in the fundus tracking will be described with reference to FIGS. 6A and 6B. When the fundus movement amount has been calculated, the correcting unit 46 moves the X-scanning scanner 53 and the Y-scanning scanner 56 so as to irradiate the position with the irradiation light, at which the scanning position has been offset by the calculated movement amount. Furthermore, when the fundus movement amount includes also the angle of the rotation direction, the correcting unit 46 also corrects the scanning direction. Thereby, in the OCT measuring system, the OCT apparatus can scan the same site as the site on the fundus Er, which has been scanned before the fundus Er moves, by using the X-scanning scanner 53 and the Y-scanning scanner 56. Regarding the timing for correcting the scanning position, each of the OCT mode and the OCTA mode will be described below.

Figure 6A:
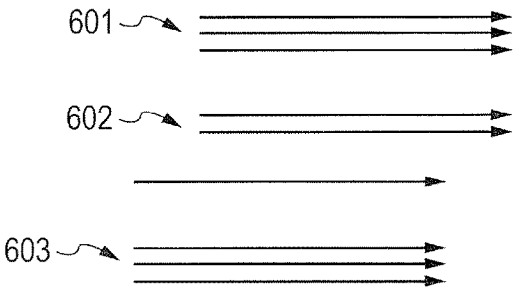
FIG. 6A is an explanatory view of correction of a scanning position in one embodiment.
Figure 6B:
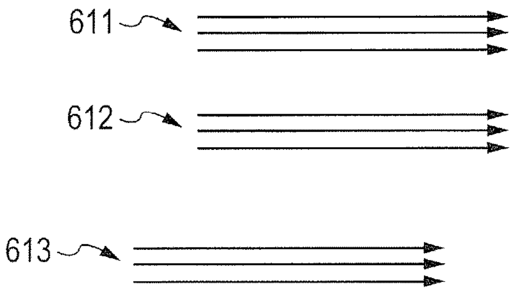
FIG. 6B is an explanatory view of correction of a scanning position in one embodiment.

FIGS. 6A and 6B illustrate examples of scanning trajectories of scanning groups 601, 602, 603, 611, 612 and 613, in the case where the scanners perform the B-scan on the same portion of the fundus Er three times respectively, in other words, in the case where m is 3. The second and third times of B-scans are illustrated to be slightly deviated from the first time of B-scan, for ease of understanding. Accordingly, for instance, the first line of B-scan in the scanning group 601 and the two B-scans below the first line of B-scan represent the B-scans at the scanning position y1 which is the same site. Incidentally, in the OCT mode, in order to reduce a noise originating in the scanning position, and the like, the OCT apparatus may perform cluster scanning by intentionally slightly deviating the scanning position. As has been described above, even though the scanning position is slightly deviated, the scanning positions shall be included in "same scanning position", in the present specification. Incidentally, in either the OCT mode or the OCTA mode, the OCT apparatus can set the scan interval between a plurality of times of scans included in the scanning group shorter than a scan interval between the last scan of a certain scanning group (first scanning group) and the initial scan of a scanning group which temporally continues to the certain scanning group (second scanning group).

An example of the correction of the scanning position by the OCT measuring system in the OCT mode will be described below with reference to FIG. 6A. FIG. 6A illustrates an example of the scanning trajectory in the case where the scanning position is corrected between an arbitrary B-scan and an arbitrary B-scan. In this case, the correcting unit 46 moves the X-scanning scanner 53 and the Y-scanning scanner 56, based on the fundus movement amount, in a time period between the second time of B-scan and the third time of B-scan in the scanning group 602, and corrects the scanning position. Thereby, even when the fundus Er has moved during imaging, the OCT apparatus can scan the same site on the fundus Er.

On the other hand, in the OCTA imaging, a problem occurs in the correction of the scanning position as illustrated in FIG. 6A. In the OCTA, the time period Δt needs to be fixed which can be spent for the scans of one scanning group (one cluster scan) including m times of scans (B-scans). This is because when the time period Δt increases, the movements of a blood flow and the fundus Er increase, which occur during the time period, and result in adversely affecting the calculation result of the correlation between the interference signals that have been obtained by m times of scans.

For instance, if the time period Δt has increased, the state of the focus changes more easily due to the movement of the fundus Er. If the mode is the OCT mode, even though the focus states of a plurality of interference signals are different, the OCT apparatus can obtain one sheet of high-definition tomogram image of which the focus states are averaged by Intensity averaging processing. However, in the case where a plurality of interference signals having different focus states are used in the OCTA mode, the difference between the focus states is calculated as the degradation of the correlation between the interference signals, and the image cannot clearly extract the vessel, which results in adversely affecting the image quality of the OCTA image. Besides the change of the focus state, the correlation decreases due to various influences such as vignetting of the light flux due to the pupil and the eyelashes, and the loss of the interference signal due to the clouding of the cornea, the crystalline lens and the vitreous body. Accordingly, in the OCTA, the time period Δt needs to be as short as possible and to be a fixed time period.

However, when the correcting unit corrects the scanning position in the tracking operation of the fundus Er, the X-scanning scanner 53 and the Y-scanning scanner 56 need a certain time period for moving. Therefore, if the correcting unit performs the tracking operation of the fundus Er while the scanning unit performs scanning of one scanning group including the m times of scans, the time period Δt for performing one cluster scanning does not become constant. Accordingly, in the OCTA mode, the correcting unit should not correct the scanning position within the scans of one scanning group including the m times of scans.

An example in which the correcting unit corrects the scanning position using the OCT measuring system in the OCTA mode will be described below with reference to FIG. 6B. FIG. 6B illustrates an example of the scanning trajectories in the case where the correcting unit corrects the scanning position only at a switching time between a certain scanning group (3 times of B-scans) and the next scanning group (3 times of B-scans). In the example illustrated in FIG. 6B, the scanning position is corrected at the switching time between the third time of B-scan of the scanning group 612 and the first time of B-scan of the scanning group 613. Even when the acquiring unit has detected the movement of the fundus Er during the second time of B-scan of the scanning group 612, the correcting unit does not correct the scanning position until the third time of B-scanning is completed, and corrects the scanning position before the first time of B-scan in the next scanning group 613 starts. Thereby, in any of the B-scans in the scanning groups 611, 612 and 613, the time period required for the three times of B-scans becomes constant, and the correcting unit can correct the scanning position without adversely affecting the image quality of the OCTA.

When the correcting unit corrects the scanning position as in the above way, in the OCTA mode, a time period to be spent from the time when the acquiring unit has detected the movement of the fundus Er to the time when the correcting unit corrects the scanning position becomes longer than that in the OCT mode. However, the movement of the fundus Er occurring during the time period is sufficiently small in many cases, and accordingly the correcting unit can correct the movement of the fundus Er at least in the B-scan direction, by the alignment of the images in the step S408 in FIG. 4 of the above described interference signal processing.

Incidentally, even in the case where the OCT apparatus uses the scan pattern of the cross scan in the OCTA mode, the correcting unit does not correct the scanning position during the cluster scan, and corrects the scanning position when the scanning unit performs the subsequent cluster scan, similarly to the above description. In other words, in this case, the correcting unit does not correct the scanning position in between the scanning groups in scanning positions on one side of the cross scan, and corrects the scanning position before the first B-scan of the scanning group in scanning positions on the other side starts. Thereby, the time period Δt can be kept constant, and the correcting unit can correct the scanning position according to the movement of the fundus Er, without adversely affecting the image quality of the OCTA.

[Rescan]

As has been described above, even when there has been a movement of the fundus Er, the OCT apparatus can continue scanning the same site of the fundus Er by correcting the scanning position. However, when the fundus Er has rapidly and largely moved during imaging, there are some cases where only correction of the scanning position is insufficient. This is because the scanning position is corrected after the fundus Er has moved and accordingly the scanning position is not corrected while the fundus Er is moving. On the other hand, in the present embodiment, when the movement of the fundus Er is rapid and large, the correcting unit 46 of the computer 40 controls the X-scanning scanner 53 and the Y-scanning scanner 56 so that the scanners rescan the scanning position which the scanners have been scanning when the movement of the fundus Er has occurred.

A reasonable range for performing the rescan is calculated from the movement amount calculation rate for the fundus Er and the B-scan rate by the scanning unit of the OCT measuring system. The frame rate of the fundus image of the SLO measuring system depends on the driving speeds of the X-scanning scanner 83 and the Y-scanning scanner 86. Acquiring one frame of the fundus image in the present embodiment requires approximately 50 milliseconds. The calculation time period required for calculating the movement amount of the fundus Er is sufficiently short as compared with 50 milliseconds, and accordingly it may be considered that the movement amount of the fundus Er is calculated every 50 milliseconds. On the other hand, the time period required for the B-scan depends on the required time period per A-scan and the number of A-scans. In the present embodiment, the A-scan spends approximately 10 microseconds per scan, and the B-scan consists of 1000 A-scan. Therefore, the time period required for the B-scan is approximately 10 milliseconds. Accordingly, in the present embodiment, the B-scan is executed approximately five times while the computer once calculates the movement amount of the fundus Er from the observation image of the SLO.

Figure 7A:
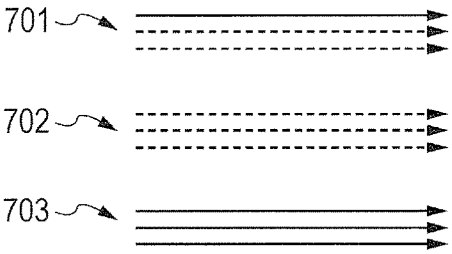
FIG. 7A is an explanatory view of rescan in one embodiment.
Figure 7B:
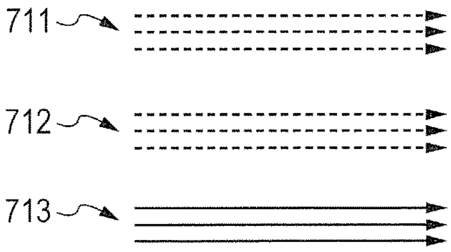
FIG. 7B is an explanatory view of rescans in one embodiment.

The rescan in the OCT mode and the OCTA mode will be described below with reference to FIGS. 7A and 7B. FIGS. 7A and 7B illustrate the scanning groups 701, 702, 703, 711, 712 and 713 at the time when m is set at 3. In FIGS. 7A and 7B, the B-scan for the rescan is expressed by a dotted line.

With reference to FIG. 7A, an example will be described in which the scanning unit performs the rescan in the OCT measuring system in the OCT mode. In the example illustrated in FIG. 7A, the movement of the fundus Er has occurred in between the second time of the scanning group 701 and the third time of the scanning group 702, and accordingly five times of B-scans in the meantime become a target for the rescan.

However, in the OCTA mode, a problem occurs in this rescan. This is because it is necessary in the OCTA mode to perform m times of B-scans during the fixed time period Δt, as has been described above. When the scanning unit performs the rescan in the OCTA mode as illustrated in FIG. 7A, the scanning time of the first time of B-scan in the scanning group 701 and the scanning time of the second and third times of B-scans are greatly different, and accordingly the time period Δt for scanning one scanning group becomes long to a large extent.

Here, consider the case, for instance, where a state of the focus on the eye to be inspected changes between the scanning time of the first time of B-scan in the scanning group 701 and the scanning time of the second and third times of B-scans. In this case, the interference signal that the computer has acquired due to the first time of B-scan and the interference signals that the computer has acquired due to the second and third times of B-scans become greatly different, which adversely affects the correlation among the interference signals.

With reference to FIG. 7B, an example of the case will be described where the scanning unit performs the rescan in the OCT measuring system in the OCTA mode. Even in the case where the movement of fundus Er has occurred in between the second time of B-scan of the scanning group 701 and the third time of B-scan of the scanning group 702, the rescan results in starting from a target that is the first time of B-scan of the scanning group 701. As has been described above, in the OCTA mode, when one part out of the m times of B-scans in one scanning group has become a target of the rescan, the scanning unit rescans the positions of all the m times of the B-scans.

The imaging time period becomes long when the rescan is performed, but the OCT apparatus can prevent an elongation of the imaging time period, by appropriately setting a threshold value of the movement amount of the fundus Er, for determining whether or not the scanning unit should perform the rescan.

[Flow of Tracking Control]

Figure 8:
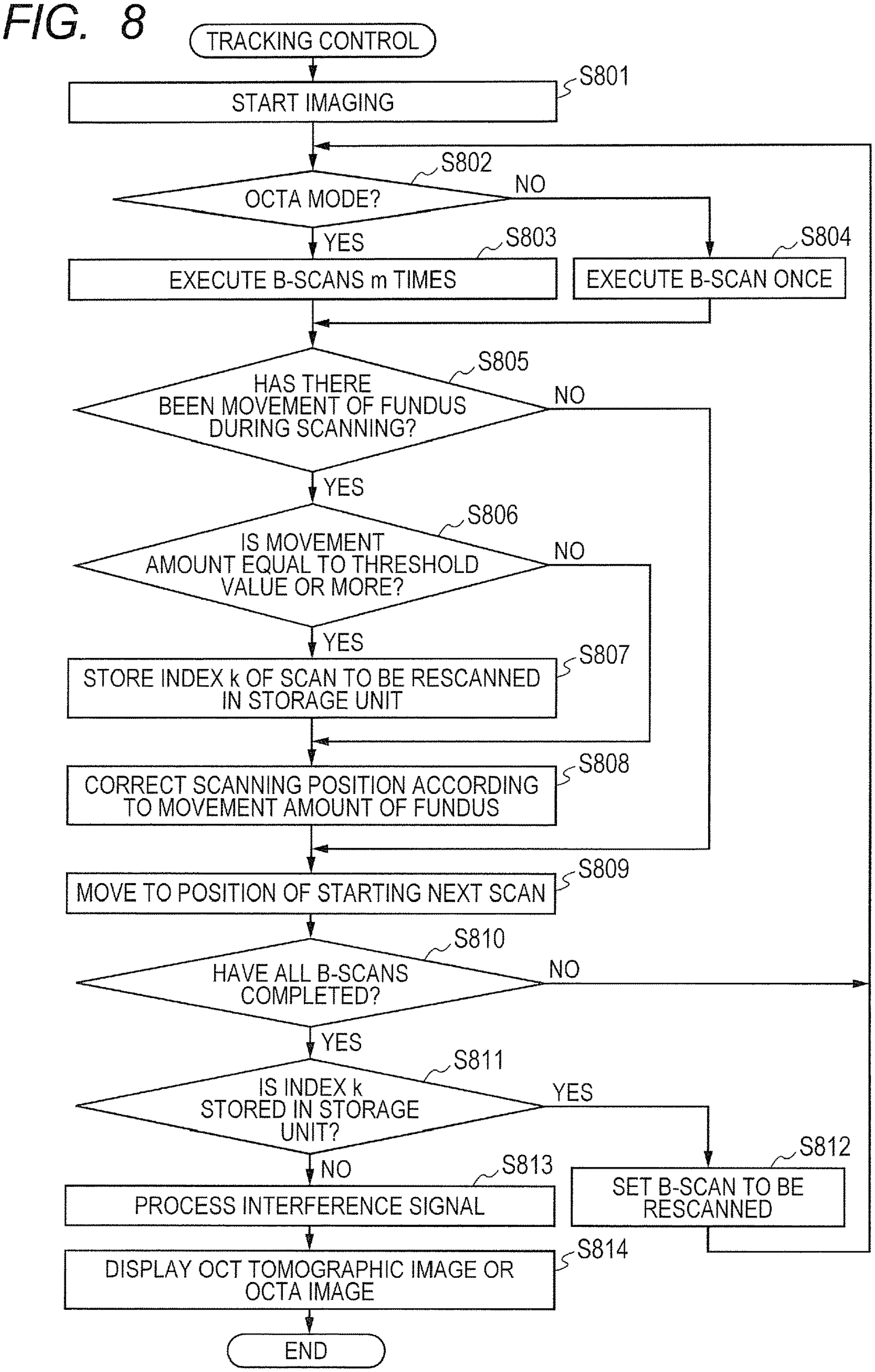
FIG. 8 is an explanatory view of fundus tracking control in one embodiment.

The flow of the correction and the rescan of the scanning position by the tracking control of the fundus Er in the OCT measuring system, which have been described above, will be described below with reference to the flowchart illustrated in FIG. 8. FIG. 8 is a flowchart illustrating the flow of the tracking control.

In a step S801, the inspector operates an unillustrated switch on the computer 40 to start imaging by the OCT measuring system.

In a step S802, the control unit 41 of the computer 40 determines whether or not the currently selected imaging mode of the OCT apparatus 100 is the OCTA mode.

When the imaging mode is the OCTA mode, the control unit 41 controls driving of the X-scanning scanner 53 and the Y-scanning scanner 56 in a step S803 to execute the B-scans m times. After this, the process proceeds to a step S805.

When the imaging mode is not the OCTA mode, in other words, is the OCT mode, the computer 40 controls the driving of the X-scanning scanner 53 and the Y-scanning scanner 56 to execute the B-scan once, in a step S804. After this, the process proceeds to the step S805.

Next, in the step S805, the control unit 41 determines whether or not the movement of the fundus Er has occurred during scanning. Here, the control unit 41 reads out the fundus movement amount that has been stored in the S503 of FIG. 5, from the storage unit 42, and determines whether the value is 0 or not. Alternatively, it is also acceptable that the control unit 41 sets a certain threshold value, and when the fundus movement amount stored in the storage unit 42 is equal to the threshold value or more, determines that there has been the movement of the fundus Er. When having determined that there has not been the movement of the fundus Er, the process proceeds to a step S809. Incidentally, the tracking control of the fundus Er illustrated in FIG. 8 and the calculation of the fundus movement amount illustrated in FIG. 5 are performed asynchronously as described above. Because of this, in the step S805, the control unit 41 can read out the latest fundus movement amount that has been acquired by the acquiring unit 45, updated by the control unit 41 and stored in the storage unit 42, and determine whether or not the movement of the fundus Er has occurred.

When having determined that there has been the movement of the fundus Er, the control unit 41 determines whether or not the fundus movement amount is equal to the threshold value or more, in a step S806. This threshold value is a threshold value for determining whether the rescan is performed or not. When the fundus movement amount is less than the threshold value, the process proceeds to a step S808.

When the fundus movement amount is equal to the threshold value or more, the control unit 41 stores the index k that indicates the scan to be rescanned, in the storage unit 42 in a step S807, in order that the scanning unit rescans the scanning position later which the scanning unit has been scanning. Here, the index k that indicates the scan to be rescanned is an index that indicates an arbitrary B-scan, in the OCT mode, and is an index that indicates the scanning group which regards the m times of the B-scans as one unit, in the OCTA mode.

In a step S808, the correcting unit 46 corrects the scanning position of the X-scanning scanner 53 and the Y-scanning scanner 56, according to the movement amount of the fundus Er. At this time, the correcting unit 46 corrects the scanning position by using the fundus movement amount which the control unit 41 has read out in the step S805. Incidentally, the data which the correcting unit 46 uses is not limited to the fundus movement amount, but may be other data concerning tracking such as a corrected value of the scanning position by the X-scanning scanner 53 and the Y-scanning scanner 56, which the control unit 41 or the like has previously determined based on the fundus movement amount.

In the step S809, the control unit 41 moves the X-scanning scanner 53 and the Y-scanning scanner 56 to the next scanning position.

In a step S810, the control unit 41 determines whether or not all the B-scans required for the imaging process have completed. When there is the B-scan that has not yet completed, the process returns to the step S802.

When all the B-scans have completed, the control unit 41 checks whether or not the index k of the scan to be rescanned is stored in the storage unit 42, in a step S811. Incidentally, when the rescan has been repeated many times, the imaging time period becomes long, and the burden on the person to be inspected increases. Accordingly, an upper limit may be set for the number of rescans. In this case, when the number of rescans has reached the upper limit, even though the index k of the scan to be rescanned is stored in the storage unit 42, the process proceeds to a step S813.

When the index k is stored in the storage unit 42, the control unit 41 sets the scan to be rescanned based on the index k, in a step S812, and returns to the step S802. When the index k is not stored in the storage unit 42, the control unit 41 performs the previously described process for the interference signals, in a step S813. Incidentally, when a plurality of indexes k are stored in the storage unit 42, the control unit 41 can set the scans corresponding to all the stored indexes k, as the scans to be rescanned.

Finally, in a step S814, the control unit 41 displays the OCT tomogram image or OCTA image which has been created in the step S813, on the screen of the display unit 70.

By performing such a control, the OCT apparatus 100 can perform the tracking operation at appropriate timing for each of the imaging modes, even when there has been the movement of the eye to be inspected during imaging. Because of this, by performing the correction or rescan of the scanning position in the above described tracking control, the OCT apparatus 100 can obtain the high-definition tomogram image and OCTA image of a desired site. Furthermore, by suitably correcting the scanning position, the OCT apparatus 100 minimizes the necessary number of times of rescans, and can prevent an imaging time period from becoming long.

As has been described above, the OCT apparatus 100 according to the present embodiment includes: the X-scanning scanner 53 and the Y-scanning scanner 56 that scan the fundus Er of the eye to be inspected with the measurement light; and an imaging mode selecting unit 43 that selects one imaging mode out of the OCT mode and the OCTA mode. In addition, the OCT apparatus 100 includes the correcting unit 46 that corrects the scanning position of the measurement light. When the OCT mode has been selected, the correcting unit 46 corrects the scanning position of the measurement light in between each of the scans, and when the OCTA mode has been selected, the correcting unit does not correct the scanning position of the measurement light in between each of the scans, and corrects the scanning position of the measurement light in between the scanning groups including a plurality of times of scans. Due to the configuration, the OCT apparatus 100 can correct the scanning position in the tracking operation at appropriate timing, for each of the imaging modes.

Furthermore, the OCT apparatus 100 includes: an OCT imaging system that generates a tomogram image of the fundus Er, based on the reference light and the returned light from the fundus Er of the measurement; and an SLO imaging system that generates the planar image of the fundus Er. In addition, the OCT apparatus 100 includes; the acquiring unit 45 that acquires the information which indicates the movement amount of the eye to be inspected, based on a plurality of planar images which have been generated by the SLO imaging system; and the storage unit 42 that stores the information therein which indicates the movement amount. Furthermore, the OCT apparatus 100 includes: the control unit 41 that updates the information which indicates the movement amount stored in the storage unit 42, every time when the information which indicates the movement amount is acquired by the acquiring unit 45. Here, when the OCTA mode has been selected, the correcting unit 46 corrects the scanning position of the measurement light in between the scanning groups, based on the information which indicates the movement amount stored in the storage unit 42, in a stage in which the last scan in the scanning group has ended. Thereby, the OCT apparatus 100 can perform the correction for the scanning position of the measurement light by the correcting unit 46, asynchronously with the acquisition of the movement amount by the acquiring unit 45. Accordingly, the OCT apparatus 100 can correct the scanning position in the tracking operation at appropriate timing for each of the imaging modes, without requiring complicated processing for synchronizing the correction of the scanning position with the acquisition of the fundus movement amount.

In addition, the OCT apparatus 100 further includes the changing unit 44 that changes at least one of the scanning range of the measurement light, the number of times of scans in the scanning group, and the scanning resolution of the measurement light, in the OCTA mode. Because of this, the OCT apparatus 100 can change the scanning range of the measurement light, the number of times of scans in the scanning group, and the scanning resolution of the measurement light, as desired by the inspector, in the OCTA mode.

Incidentally, in the present embodiment, the control unit switches the processes in the correction of the scanning position and in the control of the rescan between the OCT mode and the OCTA mode, but the present invention is not limited to this method. For instance, even in the OCT mode, the control unit may give greater importance to the scanning time period and the correlation in the same site depending on the scan pattern, and control the correcting unit so as not to correct the scanning position in the meantime. It is also acceptable that the control unit switches the processes in the various controls according to the mode, such as the focus control, the gate control and the screen operation, in addition to the correction of the scanning position and the rescan.

Furthermore, in the present embodiment, the fiber optical system is used which uses a coupler as a light splitting unit, but the spatial optical system may be used which uses a collimator and a beam splitter. In addition, the OCT apparatus uses the X-scanning scanner and the Y-scanning scanner which are formed of the galvanometer mirror as the scanning unit, but may compose each of the scanners of the scanning unit by using a polygon mirror, a resonance mirror or the like, for instance.

In addition, in the present embodiment, the imaging mode is divided into the OCT mode (first imaging mode) and the OCTA mode (second imaging mode), but the imaging mode is not limited to these modes. The imaging mode may be divided, for instance, into a single imaging mode (first imaging mode) that performs a single scan, and a cluster imaging mode (second imaging mode) that performs a cluster scan. In this case, the cluster imaging mode includes a mode of imaging the Intensity averaged image by performing the cluster scan, in addition to the mode of imaging the OCTA image. In the mode of imaging the Intensity averaged image, the control unit can generate the tomogram image of the fundus Er, by averaging the sum of a plurality of interference signals based on the reference light and the returned lights from the fundus Er of the measurement light, which have been obtained by a plurality of times of scans included in the scanning group. Also in this case, as in the above described case, the OCT apparatus performs the tracking in between the B-scans, in the single imaging mode, and performs the tracking operation in between the scanning groups, in the cluster imaging mode. Thereby, the OCT apparatus can correct the scanning position in the tracking operation at the appropriate timing for each of the imaging modes. Incidentally, when using the scan pattern of the cross scan in the cluster imaging mode, the OCT apparatus can show a similar effect, by performing the process of correcting the scanning position concerning the cross scan in the previously determined OCTA mode.

As has been described above, the present invention can provide an optical tomographic imaging apparatus and an imaging method that correct a scanning position in the tracking operation for each imaging mode at appropriate timing.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-046795, filed Mar. 10, 2016, which is hereby incorporated by reference herein in its entirety.

What is claimed is:

1. An ophthalmologic apparatus comprising:

a scanning unit arranged to scan a fundus of an eye to be inspected, with measurement light;

a selecting unit configured to select one imaging mode out of a first imaging mode and a second imaging mode which is different from the first imaging mode, wherein a plurality of times of scans included in a scanning group are executed by the scanning unit in the second imaging mode;

an acquiring unit configured to acquire information which indicates a movement amount of the eye to be inspected, based on a plurality of planar images of the fundus; and a correcting unit configured to correct a scanning position of the measurement light in an initial scan which is executed after the information indicating the movement amount has been acquired, in a case where the first imaging mode has been selected, and correct the scanning position of the measurement light in an initial scan included in an initial scanning group which is newly executed after the information indicating the movement amount has been acquired, in a case where the second imaging mode has been selected, wherein the correcting unit is configured to not correct the scanning position of the measurement light in a scan other than the initial scan in the initial scanning group, in the case where the second imaging mode has been selected.

2. The ophthalmologic apparatus according to claim 1, further comprising:

a storage unit configured to store the information indicating the movement amount; and a storage control unit configured to update the information stored in the storage unit, every time when the information is acquired by the acquiring unit, wherein if the second imaging mode has been selected, the correcting unit corrects the scanning position of the measurement light in the initial scan included in the initial scanning group, based on the information which is stored in the storage unit in the stage in which a last scan in a previous scanning group has ended.

3. The ophthalmologic apparatus according to claim 1, further comprising:

a changing unit configured to change at least one of the scanning range of the measurement light, the number of times of scans in the scanning group and the scanning resolution of the measurement light, in the second imaging mode.

4. The ophthalmologic apparatus according to claim 1, wherein the second imaging mode is a mode that images an OCTA (Optical Coherence Tomography Angiography) image, and the first imaging mode is a mode that images an image other than the OCTA image.

5. The ophthalmologic apparatus according to claim 4, wherein in the second imaging mode, the OCTA image is generated on the basis of a plurality of interference signals based on reference light and returned lights from the fundus of the measurement light, which have been obtained by the plurality of times of scans included in the scanning group.

6. The ophthalmologic apparatus according to claim 1, wherein in the second imaging mode, a tomogram image of the fundus is generated by averaging of a sum of a plurality of interference signals based on reference light and returned lights from the fundus of the measurement light, which have been obtained by the plurality of times of scans included in the scanning group.

7. The ophthalmologic apparatus according to claim 1, wherein a scan interval between the plurality of times of scans included in the scanning group is shorter than a scan interval between a last scan of a first scanning group and an initial scan of a second scanning group that temporarily continues to the first scanning group.

8. An imaging method for imaging a fundus of an eye to be inspected comprising:

scanning the fundus of the eye to be inspected with measurement light;

selecting one imaging mode out of a first imaging mode and a second imaging mode which is different from the first imaging mode, wherein a plurality of times of scans included in a scanning group are executed in the scanning in the second imaging mode;

acquiring information which indicates a movement amount of the eye to be inspected, based on a plurality of planar images of the fundus;

correcting a scanning position of the measurement light in an initial scan which is executed after the information indicating the movement amount has been acquired, in a case where the first imaging mode has been selected; and correcting the scanning position of the measurement light in an initial scan included in an initial scanning group which is newly executed after the information indicating the movement amount has been acquired, in a case where the second imaging mode has been selected, wherein the scanning position of the measurement light in a scan other than the initial scan in the initial scanning group is not corrected, in the case where the second imaging mode has been selected.

* * * * *